United States Patent [19]

Dounce et al.

[11] 4,379,965
[45] Apr. 12, 1983

[54] CONTACT LENS DISINFECTING APPARATUS

[75] Inventors: George H. Dounce, Rochester; John A. Moore, Wyoming, both of N.Y.

[73] Assignee: Bausch & Lomb Incorporated, Rochester, N.Y.

[21] Appl. No.: 252,643

[22] Filed: Apr. 9, 1981

[51] Int. Cl.³ ............................. A61L 2/18; H05B 3/06
[52] U.S. Cl. ....................................... 219/521; 219/438; 219/505; 219/536; 219/541; 422/300
[58] Field of Search ............................... 422/164–166, 422/292, 300, 302, 307; 219/385, 386, 415, 419, 433, 436, 438, 441, 439, 442, 504, 505, 521, 536, 541, 462

[56] References Cited

U.S. PATENT DOCUMENTS

| | | | |
|---|---|---|---|
| 3,414,704 | 12/1968 | Flanagan | 219/505 |
| 3,425,336 | 2/1969 | Bufkin et al. | 219/442 |
| 3,674,983 | 7/1972 | Hurko et al. | 219/436 |
| 3,720,807 | 3/1973 | Ting | 219/386 |
| 3,778,594 | 12/1973 | Wightman | 219/442 |
| 3,983,362 | 9/1976 | Hoogesteger et al. | 422/300 |
| 3,995,141 | 11/1976 | Vieau et al. | 219/441 |
| 3,996,447 | 12/1976 | Bouffard et al. | 219/505 |
| 4,039,777 | 8/1977 | Baker | 219/442 |
| 4,158,126 | 6/1979 | Seitz | 219/439 |
| 4,160,152 | 7/1979 | Wightman et al. | 219/438 |
| 4,164,645 | 8/1979 | Dogliotti | 219/441 |
| 4,242,572 | 12/1980 | Thomas et al. | 219/521 |

*Primary Examiner*—David L. Lacey
*Attorney, Agent, or Firm*—Bernard D. Bogdon; John S. Norton

[57] ABSTRACT

A contact lens disinfector utilizes a positive temperature coefficient (PTC) element as its heating source. The PTC heater element is held in intimate contact with a heat sink by a spring biasing member which accurately positions and tensions the PTC heater element thereby insuring that sufficient heat is delivered to the carrying case so that proper disinfecting of the contact lenses takes place.

13 Claims, 5 Drawing Figures

CONTACT LENS DISINFECTING APPARATUS

BACKGROUND OF THE INVENTION

1. Field of the Invention

The present invention is directed toward contact lens disinfecting apparatus, and more particularly contact lens disinfecting apparatus which feature the use of a positive temperature coefficient (PTC) heater element for imparting the proper disinfecting heat to the contact lenses.

2. Description of the Prior Art

Contact lens disinfecting units which are in common use today generally include a lens carrying case that is placed in intimate engagement with a heat dispersing plate. Close proximity to an electrically energized heater provides heat to the plate which in turn heats the contact lens carrying case by conduction and the lenses carried within to a predetermined temperature for a period of time sufficient to properly disinfect the lenses. When this period of time elapses the disinfecting unit shuts off and the current flow to the heater is terminated. The contact lens carrying case, after being allowed to cool for a period of time may then be removed and the contact lenses inserted in the user's eyes.

Generally, then, many of the contact lens disinfectors presently known apply electric current to a heating element which heats a heat dispersing plate, which in turn applys heat to a contact lens carrying case. The electrical current is generally controlled by a thermostatic switch which is used to determine when the heater reaches a certain preselected temperature. Once the temperature of the heater reaches the preselected point, the thermostatic switch opens, thereby breaking the flow of electrical current to the heater. At this time the contact lenses within the carrying case may have been exposed to sufficient heat for the required period of time to insure that they are properly disinfected or, the lens carrier may remain in contact with the heater for a period of time after the current is shut off to insure that proper disinfecting takes place. In some instances, the thermostatic switch may also control a light which is wired in series with the switch and in parallel with the heater. The light would be lit when the switch is closed and current is flowing to the heater. When the thermostatic switch senses that the preselected temperature has been reached, it opens shutting off the current to the heater and the light as well.

As in any electrical appliance, however, the more components used in its manufacture the greater is the chance that failure may occur in one, or more, of the components resulting in erratic behavior or complete breakdown of the unit. Also, the more components used in a product the more costly it becomes. Still further, when more components are used there is the associated risks that manufacturing difficulties will arise.

A contact lens disinfector which uses the above-mentioned thermostatic switch to control the flow of electricity to the heater suffers from the inherent possibility that the switch may fail, which in turn would cause the unit to fail. The switch could fail by either not opening or not closing. If the switch fails to open, the disinfecting unit presents a very definite hazard (in the absence of a thermal limiter fail-safe device) in that possible damage to the lenses could occur or, far more serious, fire could result. If the thermocouple switch fails to close, the unit would simply fail to operate and the user's lenses would not be properly disinfected.

Various issued U.S. patents disclose contact lens disinfectors which incorporate some, or all, of the above discussed features. U.S. Pat. Nos. 4,044,226 issued Aug. 23, 1977 to J. Kadlecik et al, 4,158,126 issued June 12, 1979 to L. J. Seitz, 4,178,499 issued Dec. 11, 1979 to J. G. Bowen, 4,235,842 issued Nov. 25, 1980 to M. D. Thomas et al and 4,242,572 issued Dec. 30, 1980 to M. D. Thomas et al, are some of these.

A number of U.S. patents have also been issued which disclose a number of ways to provide heat into food stuffs or liquids. Some of the patents exemplary of this type of warmers known to use a PTC heater are U.S. Pat. Nos. 3,720,807 issued Mar. 13, 1973 to Youn H. Ting, 3,876,861 issued Apr. 8, 1975 to J. W. Wightman et al, 3,995,141 issued Nov. 30, 1976 to D. P. Vieau et al and 4,160,152 issued July 3, 1979 to J. W. Wightman et al.

SUMMARY OF THE INVENTION

The present invention provides a heating apparatus for disinfecting contact lenses contained within a lens carrying case. The contact lens disinfector includes a housing, a heat sink, a positive temperature coefficient (PTC) heater element for providing and controlling the heat of the heat sink and spring biasing means for holding the PTC heater element against and electrically connecting it to the heat sink.

The contact lens disinfecting apparatus of the present invention, would have a suitable contact lens carrying case placed in the housing so as to be in direct contact with the heat sink. The unit would then be electrically energized by simply plugging it into any convenient electrical supply, such as, for instance, a 120V house circuit which would automatically start the unit. Alternatively, the unit may be started by plugging it in and then setting a manual switch. In either case the electrical current would then flow to the PTC heater element which is spring biased against, and electrically connected to, the heat sink. The characteristics of the PTC heater element are such that its temperature rises sharply until a preset temperature is achieved and then essentially maintains that temperature within close tolerances indefinitely or until the unit is disconnected from the source of electrical energy. The PTC heater element transfers the heat to the heat sink which in turn heats the carrying case and the contact lenses contained in the carrying case. The lenses are, therefore, subjected to the preset temperature for a period of time sufficient to disinfect them. This period of time may be controlled by the user simply turning the apparatus off after a certain amount of time has elapsed, or the unit may be automatically controlled by any appropriate mechanism which would shut off the flow of electricity to the PTC heater element when the preset period of time has elapsed.

A more detailed explanation of the characteristics of PTC heating elements may be found in "Self Regulating PTC Heating Systems - A New Approach for Electric Heating Appliances" by Youn H. Ting of the Control Products Division, Texas Instruments Incorporated, Attleboro, Massachusetts 02703. This paper was recommended for presentation by the IEEE Domestic Appliance Technical Committee at the 22nd Annual Appliance Technical Conference held in Chicago, Illinois on May 4–5, 1971.

DETAILED DESCRIPTION OF THE PREFERRED EMBODIMENT

Figure 1:
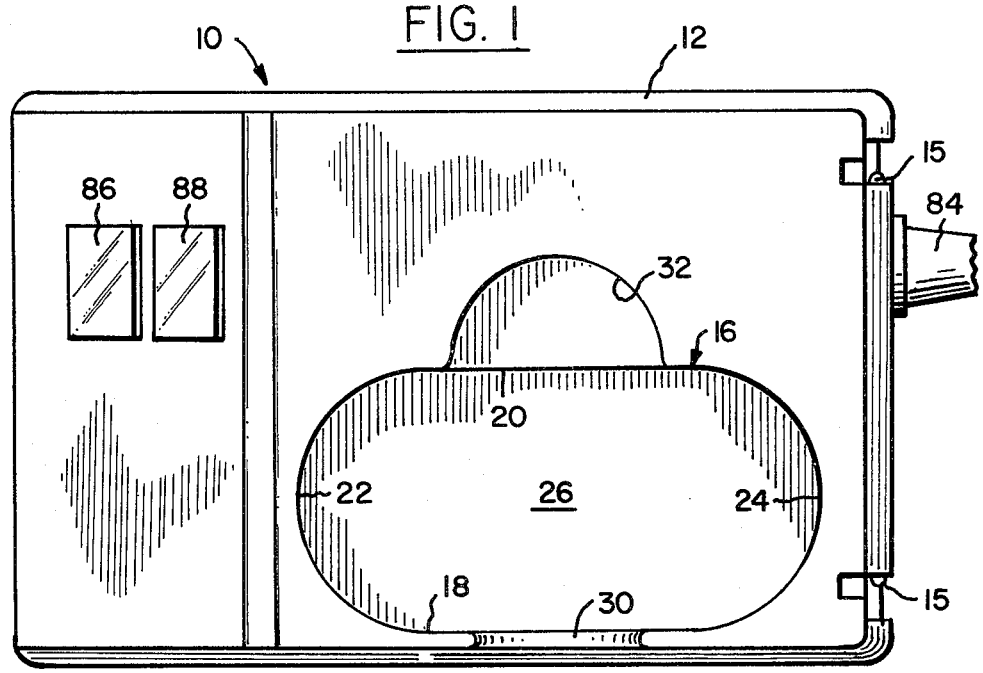
FIG. 1 is a top plan view of a contact lens disinfector having its hinged cover removed embodying the principles of the present invention.

Referring now to the drawing figures, a contact lens disinfector 10 includes a housing 12 having a top cover 14 which may be hinged at pivots 15 so that it is rotatable toward and away from housing 12. A well 16 is formed in the housing 12 and has side walls 18 and 20 which are joined by, and continuous with, end walls, which may be curved, 22 and 24, respectively. Further, the well 16 has a bottom plate 26, which is integrally formed with the side and end walls, for support of a contact lens carrying case 28, shown in FIG. 2. Defined in side walls 18 and 20 are access apertures 30 and 32, respectively, which are provided so that the user may have easy finger access to the contact lens carrying case 28 when it is in place in the well 16 and the hinged cover 14 is in the open position, as shown in FIG. 2.

Figure 4:
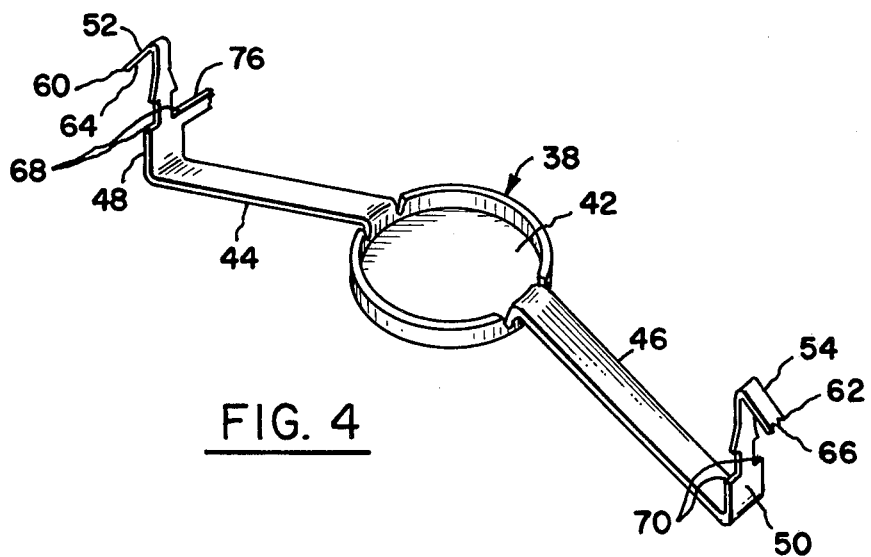
FIG. 4 is a perspective view of the spring biasing member employed in the present invention.

Disposed in direct contact with the underside 34 of bottom plate 26 is a heat sink 36 which has been found to perform satisfactorily if manufactured from, for instance, zinc coated steel. A spring biasing member 38 supports a PTC heater element 40 in a recess, 42 which is formed approximately at the center of the spring 38. The spring biasing member 38 is elongated and has a pair of legs 44 and 46 which slope downwardly and away from the recess 42 to a point on each leg where they curve nearly perpendicularly upward to form upright struts 48 and 50 on the legs 44 and 46, respectively. The upright struts 48 and 50 terminate in tangs 52, 54, respectively, as best seen in FIGS. 2 and 4. The tangs 52, 54 are received within elongated slots 56, 58, respectively, which are formed in housing 12 adjacent curved end walls 22, 24.

The spring biasing member 38 is preferentially formed from No. 420 stainless steel which has been heat treated to a Rockwell hardness of A75-77, but can be made from any spring material which will impart the required pressure to the PTC heater element 40 against the metal heat sink 36. The pressure which would be exerted by the spring 38 against the PTC heater element 40 and the heat sink 36 should be sufficient to insure that proper electrical contact would be made between the PTC heater element 40 and the metal heat sink 36. It has been found that by applying approximately 10 psi to the PTC heater element 40 by the spring 38 that an electrical connection has been made which is very positive.

Figure 2:
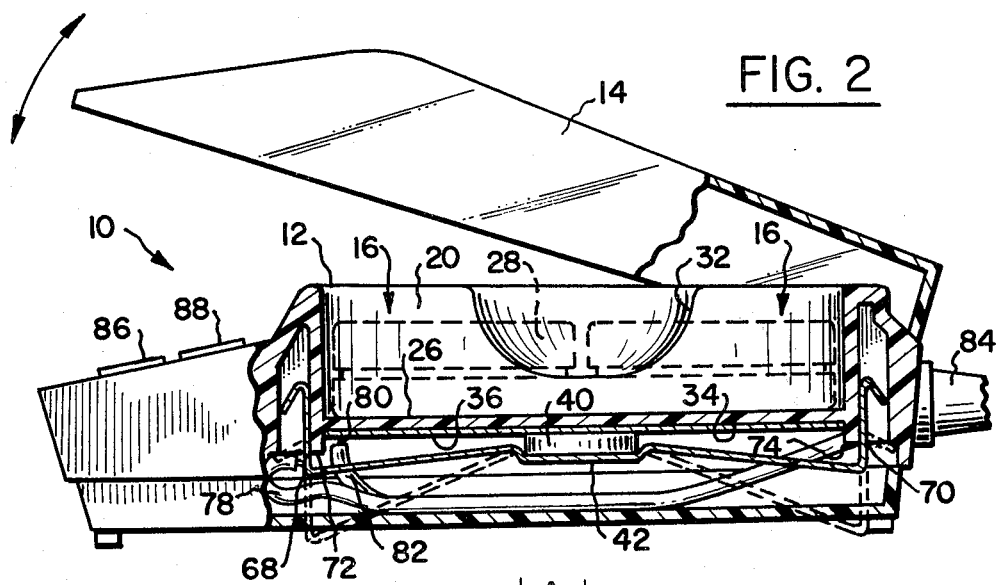
FIG. 2 is a partially sectioned side view of the disinfector of FIG. 1 having the cover in an open position.
Figure 5:
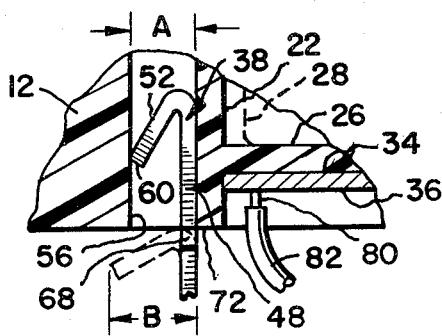
FIG. 5 is an enlarged partial view of the spring biasing member before and after insertion in the disinfector.
Figure 3:
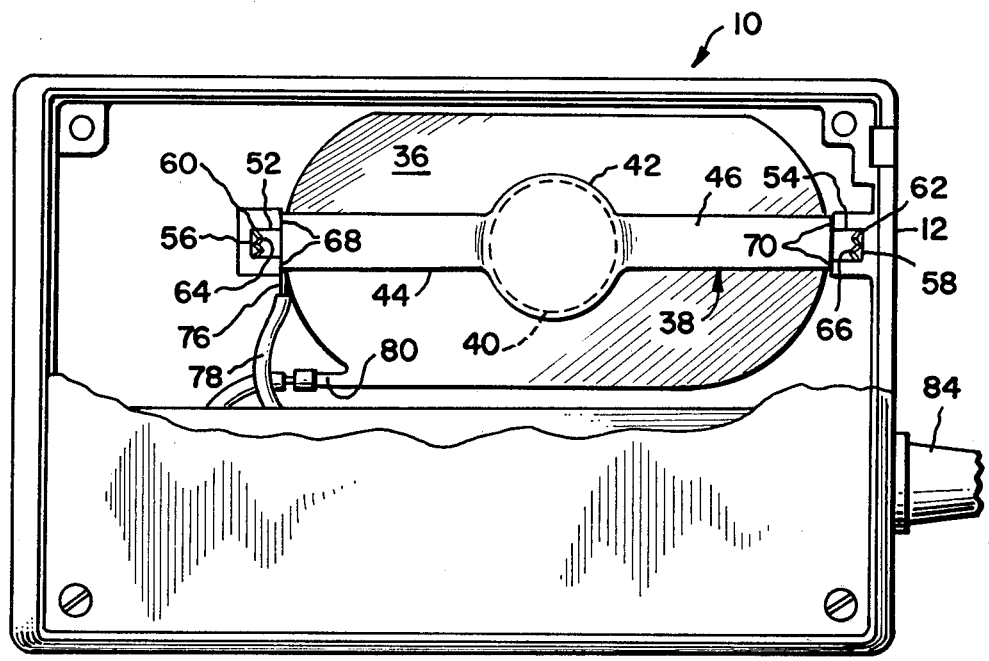
FIG. 3 is a bottom view of the disinfector partially broken away.

In order to better understand how the spring 38 cooperates with the PTC heater element 40 and the heat sink 36, particular reference should be made to FIGS. 2 and 5 of the drawings wherein the spring 38 is shown in dotted lines in its totally relaxed position before insertion into elongated slots 56 and 58 of housing 12. Also, the spring 38 is shown, by full lines, in the position it will assume once it has been placed in housing 12. By referring to FIG. 3, it is easily seen, by comparison, the amount of deflection that takes place in the legs 44 and 46. By referring to FIG. 5 the amount of deflection of the tangs 52 and 54 will be seen. It will, of course, be readily understood that the deflection of the spring 38 takes place when the unit is finally assembled.

In order to assemble the unit, the spring 38, which holds the PTC heater element 40, would be presented by any appropriate means to the housing 12 so that the tangs 52 and 54 are properly aligned with respective elongated slots 56 and 58. By referring to FIGS. 2 and 5 it will be seen that the angle that the tangs 52 and 54 make with the upright struts 48 and 50 is greater when the spring is relaxed (shown in dotted lines) than when the tangs (shown in full lines) are forced into the slots 56 and 58. This is because the dimension "A" of the slot is smaller than the corresponding dimension "B" of the relaxed tang of the spring 38. Thus, by designing the tangs 52 and 54 in such a manner, they act to exert a force against the walls of the slots 56 and 58 insuring that the spring will hold and maintain a certain position within the slots, and, accordingly, within the housing 12. Further, by designing the angle of the tangs of the spring so that they are acute, with respect to the upright struts, the tangs act as one way limiters. That is, the tangs 52 and 54 will deflect when they are pushed into the elongated slots 56 and 58, as best seen in enlarged view FIG. 5. However, should, for any unforeseen reason, a force be exerted upon the spring 38 to dislodge it from position, the tangs tend to deflect in a positive locking manner against the side walls of the elongated slots. To further insure that the spring 38 maintains its position in the housing 12 the ends 60 and 62 of tangs 52 and 54, respectively, may have serrations 64 and 66 formed thereon, as best seen in FIG. 4. These serrations would act to insure this positive positioning of the spring by literally digging into the walls of the elongated slots 56 and 58 so that the spring may not be dislodged.

The spring 38 further includes means positioned thereon for insuring that the spring may only be inserted into the elongated slots 56 and 58 of housing 12 to a preselected depth so that the amount of deflection of the spring is known and, therefore, also the pressure it will exert on the PTC heater pill 40. A shoulder, or stop member, 68 and 70 is positioned on upright struts 48 and 50, respectively. These shoulders 68 and 70, as best seen in FIG. 4, are designed to engage mating surfaces 72 and 74, respectively, of housing 12 adjacent slots 56 and 58 when the spring 38 has been inserted the proper distance into the slots. When the shoulders 68 and 70 bottom against mating surfaces 72 and 74, the legs 44 and 46 of spring 38 will have been caused to deflect to a predetermined amount, as shown in full lines in FIG. 2. The amount of deflection in turn translates into the amount of pressure that the spring will exert against the PTC heater pill 40. The amount of pressure can, therefore, be fairly accurately guaged and a positive electrical connection can be made between the PTC heater element 40 and both the heat sink 36 and the spring 38.

The electrical connection between the PTC heater element 40 and the heat sink 36 can be made in any convenient manner. It has been found, for instance, appropriate to provide a tang 76, as best seen in FIG. 4, on the spring 38 to which one electrical lead 78 may be attached. A second tang 80 may be provided on heat sink 36, as best seen in FIG. 2 to which the second electrical lead 82 would be connected. These electrical leads would be subsequently connected, such as, for instance, by cord 84 to any appropriate 120 V source of electrical energy. In certain instances it may be desirable to connect the cord to, for example, a 12 volt source. This would, of course, depend on the characteristics of the PTC heater element 40.

In operation then, the user would open hinged cover 14 thereby exposing well 16. The contact lens carrying case 28 would be placed in the well 16, the access slots 30 and 32 allowing for relatively unencumbered finger movement by the user. The carrying case would be supported by, and in positive engagement with bottom plate 26 of the well 16.

In the disinfector's simplest form, the hinged cover would then be closed over the housing 12 so as to enclose the carrying case 28. The power supply cord 84 would then be plugged into any appropriate source of electrical energy. The PTC heater element 40 would, consequently, become energized by the flow of electrical current through, for instance, lead 78 to spring 38 through the PTC heater element and to the lead 82 on heat sink 36. The characteristics of the PTC heater element 40 are such that its temperature would rise rapidly until a preselected temperature has been reached. Once the desired temperature has been reached the PTC heater element 40 will maintain that temperature indefinitely or until the source of electrical energy is disrupted.

The PTC heater element 40 in turn conducts heat to the heat sink 36 which has been dimensioned to closely approximate the dimensions of bottom plate 26 of the well 16. The heat sink 36 is positioned, as hereinabove described, to be in intimate contact with the bottom plate 26 so that when the heat sink 36 becomes heated by the PTC heater elements 40 it will conduct heat evenly through the bottom plate 26 to the carrying case 28. The solution in the carrying case becomes heated and the contact lenses contained therein are exposed to this heat for a period of time sufficient to insure that they are disinfected. Because the bottom plate 26 is integrally formed with the walls of the well, no foreign substance may accidentally be transmitted to the heating source which thereby reduces the chance of accidental electric shock to the user.

As stated earlier in this description, the heat of disinfector 10 is automatically regulated by the PTC heater element 40. The time cycle also can be regulated by the user simply by insuring that the disinfector 10 is electrically energized for a preset period of time. Once that period of time has elapsed the user could simply unplug the unit and the lenses would be ready for wear.

If a more convenient method is desired, a manual switch 86 could be provided to initially start the heating cycle. An appropriate timing circuit could be incorporated into the electrical circuit to insure that the disinfector 10 has been electrically energized for a predetermined period of time. The timing circuit would then have the capability to shut off the flow of current. A light 88 could also be incorporated into the electrical circuit to either tell the user that the disinfector is in the heating cycle, or that the heating cycle has been completed and the lenses are disinfected.

It should be understood that while only a few embodiments of the present invention have been described, further changes or modifications can be made without departing from the spirit or scope of the invention. It is, of course, intended that any such changes which fall within the scope of the appended claims are certainly intended to be included.

It is claimed:

1. Apparatus for disinfecting contact lenses contained within a contact lens carrying case, comprising:
   a housing defining a well for supporting a contact lens carrying case, said well being defined by side walls, end walls and bottom support means for supporting and conducting heat to contact lenses contained within said carrying case;
   a heat sink positioned in said housing to directly contact said well bottom support means for conducting heat to said bottom support means;
   a PTC heater element for providing, and automatically controlling, heat supplied to said heat sink, said PTC heater element being electrically energizable and having the characteristics to initially sharply rise in temperature until a preset temperature is achieved and thereafter maintain that temperature until said PTC heater element is de-energized;
   a spring biasing member supporting said PTC heater element and locating and biasing said PTC heater element against said heat sink, including a central portion for receiving and positioning said PTC heater element in close relationship with said heat sink and a pair of extensions extending outwardly from said central portion to form legs for engagement with said housing for locating said PTC heater element relative to said housing and said heat sink; and
   locating means being defined in said housing so as to receive and engage said legs of said spring biasing member in order to cause said extensions to sufficiently flex to urge and maintain said PTC heater element in close contact with said heat sink.

2. The contact lens disinfecting apparatus as set forth in claim 1 wherein said central portion for receiving and positioning said PTC heater element of said spring biasing member is recessed to hold said PTC heater element.

3. The contact lens disinfecting apparatus as set forth in claim 1 wherein said spring biasing member includes thereon means for providing electrical energization thereto.

4. The contact lens disinfecting apparatus as set forth in claim 3 wherein said means for providing electrical energization thereto comprises a tang formed on said spring biasing member.

5. The contact lens disinfecting apparatus as set forth in claim 1, and further including cover means cooperable with said housing for enclosing the well defined therein for supporting the contact lens carrying case.

6. The contact lens disinfecting apparatus as set forth in claim 5, wherein said cover means is hinged to said housing so as to be pivotable toward or away from said housing and said well therein.

7. The contact lens disinfecting apparatus as set forth in claim 1 wherein said legs for engagement with said housing have means thereon for permanently locating said spring biasing member in said housing.

8. The contact lens disinfecting apparatus as set forth in claim 7 wherein said means for permanently locating said spring biasing member in said housing comprise tangs.

9. The contact lens disinfecting apparatus as set forth in claim 8 wherein said tangs have serrations formed thereon.

10. The contact lens disinfecting apparatus as set forth in claim 1 wherein said spring biasing member includes stop means thereon for engagement with said housing, said stop means limiting the depth to which said legs of said spring biasing member are received in said housing locating means.

11. The contact lens disinfecting apparatus as set forth in claim 10 wherein said stop means is formed on at least one of said legs.

12. The contact lens disinfecting apparatus as set forth in claim 1 wherein said locating means defined in said housing for receiving and engaging said spring biasing member legs comprise a pair of elongated slots.

13. The contact lens disinfecting apparatus as set forth in claim 12 wherein said elongated slots are located in said housing adjacent said end walls of said well.

* * * * *